(12) United States Patent
Devic et al.

(10) Patent No.: US 7,867,947 B1
(45) Date of Patent: *Jan. 11, 2011

(54) METHOD OF MAKING FERTILIZER COMBINATION PRODUCTS INCLUDING FERTILIZER GRANULES AND CELLULOSIC GRANULES CARRYING PESTICIDES AND OTHER ACTIVE INGREDIENTS

(75) Inventors: Milenko Devic, Raleigh, NC (US); Paul A. Dongieux, Jr., Oxford, MS (US)

(73) Assignee: Kadant Grantek Inc., Green Bay, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/569,546

(22) Filed: Sep. 29, 2009

Related U.S. Application Data

(62) Division of application No. 11/634,451, filed on Dec. 5, 2006, now Pat. No. 7,635,404.

(51) Int. Cl.
*C05F 11/00* (2006.01)
*C05F 11/02* (2006.01)

(52) U.S. Cl. .............................. 504/101; 71/21; 71/23; 71/24; 71/25; 71/26; 504/102

(58) Field of Classification Search ................ 504/101, 504/102; 71/21, 23, 24, 25, 26
See application file for complete search history.

(56) References Cited

U.S. PATENT DOCUMENTS

| | | | |
|---|---|---|---|
| 2,004,706 A | 6/1935 | Nuske | |
| 2,218,695 A | 10/1940 | Leatherman | |
| 3,146,087 A | 8/1964 | Formaini et al. | |
| 3,252,785 A * | 5/1966 | Hoblit | 71/23 |
| 3,533,775 A | 10/1970 | Brown | |
| 4,343,646 A | 8/1982 | Leonard | |
| 4,721,059 A | 1/1988 | Lowe et al. | |
| 4,734,393 A | 3/1988 | Lowe et al. | |
| 5,019,564 A | 5/1991 | Lowe et al. | |
| 5,401,291 A | 3/1995 | Inoue | |
| 5,730,371 A | 3/1998 | Dongieux, Jr. et al. | |
| 5,770,138 A | 6/1998 | Yoder | |
| 5,843,203 A | 12/1998 | Lindsay et al. | |
| 6,030,565 A | 2/2000 | Golan | |
| 6,194,065 B1 | 2/2001 | Golan | |
| 6,231,660 B1 | 5/2001 | Welshimer et al. | |
| 6,383,246 B1 | 5/2002 | Konishi et al. | |
| 6,613,138 B2 | 9/2003 | Welshimer et al. | |
| 6,808,557 B2 | 10/2004 | Holbrey et al. | |
| 6,884,756 B2 | 4/2005 | Lynch et al. | |
| 7,666,399 B2 * | 2/2010 | Birthisel et al. | 424/84 |
| 2003/0215657 A1 | 11/2003 | Tijsma et al. | |
| 2004/0112297 A1 | 6/2004 | Rasner et al. | |
| 2005/0166652 A1 | 8/2005 | Blount | |
| 2006/0252646 A1 * | 11/2006 | Spence | 504/101 |
| 2007/0163316 A1 * | 7/2007 | Fedkenheuer et al. | 71/11 |

* cited by examiner

*Primary Examiner*—Wayne Langel
(74) *Attorney, Agent, or Firm*—Drinker Biddle & Reath LLP

(57) ABSTRACT

Method of making blends of fertilizer granules and highly absorbent cellulosic granules carrying one or more pesticidal or other active ingredients that resist the formation of actives dust or segregation of the granules and that ensure even and efficient application of both the fertilizer and the active ingredients.

18 Claims, No Drawings

METHOD OF MAKING FERTILIZER COMBINATION PRODUCTS INCLUDING FERTILIZER GRANULES AND CELLULOSIC GRANULES CARRYING PESTICIDES AND OTHER ACTIVE INGREDIENTS

CROSS-REFERENCE TO RELATED PATENT APPLICATIONS

This application is a divisional of U.S. patent application Ser. No. 11/634,451, filed Dec. 5, 2006, now allowed, which is incorporated herein by reference in its entirety.

FIELD OF THE INVENTION

This invention is directed to a method of making improved fertilizer combination products including cellulosic granules carrying pesticidal and other active ingredients and, more particularly to a method of making generally heterogeneous blends of fertilizer granules and highly absorbent cellulosic granules carrying one or more such active ingredients.

BACKGROUND OF THE INVENTION

It is known that active pesticidal and other active ingredients can be applied to inert highly absorbent cellulosic granule carriers. Pesticides and pesticidal ingredients in this context comprise any chemical or biological agent or combination of agents that kills plant or animal pests including herbicides, fungicides and insecticides. Pesticides can be applied to such cellulosic granule carriers by spraying the active ingredients in liquid form onto the cellulosic granules so that they penetrate into the granules. So long as the level of the active ingredients does not exceed the liquid holding capacity of the granules, there is generally no need to subject the granules to a drying step following the liquid application. Also, the cellulosic granules may be dusted with pesticides and other active ingredients in powder form. The adhesion of the powders may be enhanced by the application of a liquid adherence agent such as an inert oil.

However, it has not previously been suggested that such treated cellulosic granules could be blended with fertilizer granules and applied as a blended combination product. This is because cellulosic granules are of very different densities (and often different sizes and shapes as well) than the fertilizer granules and would be expected to segregate in a combination product. Such segregation would be expected to occur during blending, bagging, storage and handling, leading to uneven distribution of the granules carrying the actives and the fertilizer granules upon application, as well as possible clogging of the application apparatus.

Nevertheless, combination products of fertilizers and pesticides and other active ingredients that are compatible with the fertilizer are used in the turf industry and elsewhere. Most commonly such combination products are made by spraying liquid pesticides and other active ingredients directly onto NPK fertilizer granules, with minimal amounts of the active ingredients being absorbed and the lion's share adhering to the surface of the fertilizer granules. Alternatively, active ingredients have been applied to the surface of inert carriers (e.g., granulated lime or clay) having a density that generally matches the density of the fertilizer granules and this generally density-matched carrier is then blended with the fertilizer granules. Unfortunately, such coatings of actives on NPK fertilizer granules or conventional inert carriers break down during blending, handling or shipping, creating a significant level of free fine particles carrying high concentrations of the active ingredients. The release of such fine particles carrying high concentrations of pesticide and other active ingredients raises worker safety concerns. The presence of such fine particles of the active ingredients also affects the uniformity of product application and hence the plant phytotoxicity of conventional combination products. There is thus a significant need for a non-segregating carrier for pesticides and other active ingredients in fertilizer combination products that, once treated with the active ingredients is substantially dust-free and doesn't break down during blending, shipping or handling to release fine particles of pesticide and other active ingredients.

One herbicide that is used in current herbicide/fertilizer combination products is oxadiazon. Oxadiazon is a pre-emergence herbicide that provides season-long broadleaf and grass control in turf, ornamental plants and agricultural crops. Current oxadiazon combination products are typically not dust-free following blending, bagging and shipping due to breakdown of the oxadiazon carrier coating, as discussed above. Unfortunately, oxadiazon dust released on application of such combination products tends to coat and adhere to leaf blades increasing the potential for leaf burn. It is thus desirable to deliver the oxadiazon on dust-free granules that will bounce off leaf blades and reach the soil surface without adhering to the leaf blades or other plant surfaces. Current approaches to address this problem have included adding dust control agents such as oils as well as desiccants and anti-clumping agents in combination with the oxadiazon carriers. Unfortunately, these approaches have yielded inconsistent efficiency, dusting, and phytotoxicity results.

Another important factor to consider when formulating pre-emergence herbicides like oxadiazon in fertilizer combination products is particle distribution on the soil surface. Optimal weed control for pre-emergent products requires adequate soil surface coverage. Unfortunately, it is difficult to apply a precise and uniform quantity of fertilizer and oxadiazon per unit area of soil surface using current combination products due to the excessive and unevenly distributed amounts of herbicide and herbicide dust that is present in the combination product.

There is thus a need for heterogeneous blends of fertilizer granules and granules carrying one or more pesticides and other active ingredients that are free of actives dust and that are not subject to segregation of the carrier and fertilizer granules or production of actives dust during blending, handling or shipping. The present invention meets these needs in a unique and unexpected way.

SUMMARY OF THE INVENTION

The present invention comprises heterogeneous blends of fertilizer granules and highly absorbent cellulosic granules carrying one or more pesticides and other active ingredients that are substantially free of actives dust and that are not subject to segregation of the carrier and fertilizer granules.

DETAILED DESCRIPTION OF THE INVENTION

The compositions of the present invention comprise blends of fertilizer granules and highly absorbent cellulosic granules carrying one or more active ingredients. Active ingredients include but are not limited to herbicides, insecticides, fungicides, wetting agents, microorganisms/micronutrients, biostimulants, root stimulants and industrial and turf related enzymes.

The cellulosic granules useful in the present invention are derived from pulp or paper sludge. The cellulosic granules may be made by first adjusting the moisture content of raw pulp or paper sludge, reducing fiber size, agitating in an appropriate device to agglomerate the cellulosic fibers present in the pulp or paper sludge to form granules, and then drying the granules. Techniques for making suitable cellulosic granules are described in U.S. Pat. Nos. 5,843,203; 5,770,138; 5,730,371; 5,019,564; 4,734,393 and 4,721,059, the entire disclosures of which are incorporated by reference. Agglomeration thus may be achieved by agitating the mixture with added water in an agglomeration device such as a drum pelletizer, disk pelletizer, pinmill, or granulator. The use of a pinmill is preferred. The fiber content of the solids in the mixture should exceed at least 10%-15% by weight and will preferably be as high as possible, with mineral fillers constituting the remainder. During agitation, the fibers begin to interlock and bond together to form the granules, the size of which is determined by the water/solids ratio, the time elapsed in the agglomeration process, and the fiber/filler ratio. The sludge and slurry mixture preferably is formed into generally spherical cellulosic pellets which are preferred in the practice of the present invention.

It is preferred that the cellulosic granules be free-flowing and of generally uniform bulk density. Unfortunately, under certain conditions, granules formed from pulp or paper sludge will have fibers protruding from their surface. The protruding fibers can cause the granules to stick together and therefore prevent them from flowing freely. The fibers also can create air pockets which make for non-uniform bulk density. Finally, protruding fibers can decrease the absorbency or liquid holding capacity of the granules because some of the liquid which otherwise would be absorbed by the granules instead adheres to the protruding fibers. Therefore, preferably the cellulosic granules used in the present invention will be tumbled in a rolling device before drying. Granules that have been treated in the rolling device are preferred in the practice of the invention because they exhibit improved generally spherical granular shape and generally uniform bulk density, a minimization of protruding fibers, enhanced flow properties and superior liquid holding capacity.

The starting material in the formation of the cellulosic granules preferably is pulp or paper sludge, although other fibrous plant materials such as vegetable fibers like sugar beet, sugar cane, citrus pulp, grain and potato, and wood flour, peat moss, composted organic materials and manures may be utilized. Other starting materials that may be included can be selected from the following non-limiting list: cotton, straw, brewers condensed solubles, lignosulfonate, sodium carbonate lignin, cane molasses, beet syrup, beet molasses, whey starch, soy solubles, corn cob, rice hulls, peanut hulls, ground wheat straw flour, wheat flour, soy flour, cellulose derivates, cellulose-based polymer binders, seed meal, feather meal, soy meal, humic acid, animal waste, activated sludge, and hydrolyzed animal hair. The starting material may also contain up to about 20% extraneous matter, such as synthetic fibers, shredded plastics and ink residues. The above materials, including pulp or paper sludge, may be used either individually or in any combination of two or more thereof.

When pulp or paper sludge is used, it may include any primary pulp or paper sludge generated by a sulfate, sulfite, de-inked, mechanical or semi-chemical pulping process either alone or in combination with a secondary sludge generated by a sulfate, sulfite, de-inked, mechanical or semi-chemical pulping process. One particularly preferred sludge is primary de-inked sludge. Primary de-inked sludge is the waste material produced from paper mills which use waste paper both pre- and post-consumer, newsprint and other papers as feedstock. The sludge has a content of about 40%-90% fiber and about 10%-60% filler (e.g. kaolin, barytes, calcium carbonate, titanium dioxide, other plant fibers, etc.).

De-inked paper sludge in its raw form is approximately 90% water. When it is used it should be analyzed for composition and bacteria and then dewatered by any accepted method (usually pressing or centrifuging) to approximately 40%-50% solids. Dewatering to 45% solids is preferred. The paper sludge is next broken down to make it a consistent size. The moisture level is adjusted, if necessary, by heating, for example in a conventional fluid bed dryer. The paper sludge is then shredded by any conventional method (e.g. high-speed intensive mixer, reduction mill or shredder) to an average fiber length of about 1-10 mm. Preferred equipment for this purpose includes a Turbulizer made by Bepex of Minneapolis, Minn. The preferred average fiber length is about 1-4 mm. The dewatered fiber then may undergo a quality adjustment, if required. This quality adjustment may involve the addition of additives such as a biocide or slimacide to control bacterial and fungal growth; kaolin clay or barytes to increase density; and, a fragrance to counteract odors.

While the active ingredients preferably will be incorporated into the granules after they are dried, the active ingredients may also be incorporated into the sludge mixture before the granules are dried, so long as the active ingredients will retain their efficacy after being subjected to the heat associated with drying.

When the preferred tumbling step is used, the granules are tumbled for a period of time ("residence time") in a separate tumbling device. The preferred residence time in the tumbling device is in the range of about 1 to 60 minutes, with a residence time of about 15 to 20 minutes being preferred. The tumbling action produces enhanced granule-against-granule interaction, which is believed to decrease or eliminate undesirable protruding fibers. The granules become rounded and more spherical in shape, as preferred in the present invention. It may be desirable to add water at a rate sufficient to increase the moisture level of the incoming granules by up to about 5% to enhance the flowability of the final product. It is preferred that the moisture level of the incoming granules be increased by approximately 1.5%.

The tumbling action may be achieved using a generally horizontal tube or rolling device that rotates about its longitudinal axis and is positioned at a slight angle of about 1-5 degrees to facilitate the flow of the granules onto the discharge belt, as described in U.S. Pat. No. 5,770,138. The diameter and length of the rolling device are dependent upon the scale of operation and the type of sludge used. Also, it is preferred that the rolling device have a generally smooth inner surface.

The resulting rolled product is dried until the granule contains 1%-10% moisture by weight. Drying is accomplished in any standard dryer such as a fluid bed dryer, turbo dryer, belt dryer or tray dryer at a temperature range of about 200-750° F. After drying, color may be added.

Preferred carrier granules used in the compositions of the present invention are agglomerated cellulosic granules sold by Kadant Grantek, Inc. of Green Bay, Wis. under its trademark BIODAC®. These and other agglomerated cellulosic granules suitable to the practice of the present invention preferably contain at least 30% by weight cellulosic fibers and more preferably contain at least about 50% by weight cellulosic fibers. Cellulosic granules comprising any size combination between about 60 and 4 mesh may be used. For example, any one or combinations of two or more of BIODAC® 4/8, 4/30, 10/30, 12/20, 16/30, 20/50, and 30/60, (in which the numbers represent the upper and lower U.S. mesh size of the two screens used), are all known to work in the present application. Cellulosic granules in the size range of about 10/30 mesh are preferred. Preferably, the cellulosic granules will have density of about 30-48 pounds per cubic foot.

The weight ratio of the active ingredient in liquid form to the carrier granule should be about 0.01-25% by weight and preferably will be from about 2 to 10% by weight. The active ingredient is the formulation excluding liquid diluent, wetting agents and any other adjuvants.

We turn now to the fertilizer component of the compositions of the invention. Fertilizer in granular form has long been preferred because of advantages in the uniformity of dissemination of granulated fertilizer. Fertilizer granulation can be achieved in any acceptable way. For example, granular fertilizers can be produced through a chemical reaction in which heat is generated to produce granulation into a solid form of a liquid fertilizer (e.g., sulfuric and/or phosphoric acid or ammonia). In another approach, a swelling clay may be blended with liquid elemental sulfur and then solidified to create a controlled release sulfate fertilizer. The presence of the swelling clay in the solid sulfur particle accelerates the breakdown of the sulfur into a small particulate size distribution that favors subsequent microbiological conversion of the sulfur to the plant nutrient sulfate.

In yet another approach, encapsulated slow release fertilizers have been developed using solvent-applied polymer coatings. For this type of encapsulated fertilizer, the polymer is first dissolved in an organic solvent and then applied to a fertilizer base in either a coating drum or a fluid bed. As the solvent evaporates, a uniform, continuous polymer film is left behind, forming an encapsulating coating. Finally, latex coated fertilizers can be produced by first applying a sodium silicate precoat to a fertilizer core to protect it from dissolution caused by the water-borne latex. After precoating is completed, a high molecular weight polymer latex top coat is applied to the precoated fertilizer core. As the water from the latex evaporates, a continuous film, similar to that left behind during solvent-applied polymer coating, is left surrounding the fertilizer granule.

As an example, granular and NPK-containing fertilizers typically ranging in SGN sizes from about 100 to 260 and in densities from about 50 to 60 lbs./ft.$^3$ or higher can be used. Any available fertilizer, in prilled or granulated form may be used. (In the context of the present invention prilled and granulated fertilizers are referred to generally as fertilizer "granules".) For example, the fertilizer granules can be made from one or more of the following: urea, potash, sulfur/swelling clay matrices, micronutrient fertilizers, sulfur-coated urea, isobutylidene diurca, ammonium nitrate, ammonium sulfate, ammonium phosphate, triple super phosphate, phosphoric acid, potassium sulphate, potassium nitrate, potassium metaphosphate, potassium chloride, dipotassium carbonate, potassium oxide and combinations thereof.

The combination products of the present invention may be prepared by any convenient means. For example, granules carrying the pesticide or other active ingredient may be prepared by spraying the cellulosic granules with one or more liquid active ingredients at a level up to the liquid holding capacity of the cellulosic granules. The liquid in this case will include the actives component, diluents and adjuvants as appropriate. Once prepared, the resulting cellulosic granule carriers can then be back-blended with the fertilizer granules to form a uniform mixture of the cellulosic and fertilizer granules.

In an alternate and preferred method, the cellulosic granules and the fertilizer granules will first be uniformly blended and then the blend will be sprayed with the liquid pesticide or other actives ingredient. Surprisingly, it has been found that the cellulosic granules selectively absorb the liquid and little or no actives remain on the fertilizer granules. Following this, the combination product may be sprayed with an oil such as white mineral oil which will selectively adhere primarily to the fertilizer granules, creating a coating that resists fertilizer dust formation.

In another, but less preferred alternative, the active ingredients may be applied to the cellulosic granules in dried powder form by, for example, dusting the powder onto the surface of the cellulosic granules. In this case, it is preferred that after the dusting application, the granules are sprayed with an adherent liquid such as an oil (e.g., white mineral oil) that soaks into the surface of the cellulosic granules and retains the powder to minimize later formation of fines. The powder coated cellulosic granules may then be back-blended with the fertilizer granules.

The combination products of the present invention preferably include about 5 to 90% by weight cellulosic granules treated with pesticide or other active ingredients and about 95 to 10% by weight fertilizer granules. More preferably, the composition will include about 10 to 20% treated cellulosic granules and about 90 to 80% by weight fertilizer granules.

Any herbicide that is compatible with the cellulosic granules can be used in the practice of the present invention. For example, any one of the following herbicides could be used: benefin, flumioxazin, dithiopyr, oxadiazon, pendimethalin, penoxsulam, trifluralin and trifluralin/benefin. Among these, oxadiazon is currently preferred.

Suitable fungicides for use in the practice of the invention include any fungicide compatible with the cellulosic granules. For example, fungicides compatible with the cellulosic granules that can be used include, but are not limited to, the following: azoxystrobin, tebuconazole, or propiconazole. Among these azoxystrobin is currently preferred.

Insecticides that can be used in the practice and invention include any insecticide compatible with the cellulosic granules. For example, insecticides that can be used include, but are not limited to, the following: bifenthrin, cadusafos, cyfluthrin, chloropyrifor, ethoprop, fipronil, halofenozide, imidacloprid, methoprene, permethrin, phorate, temephos and terbufos. Among these fipronil is currently preferred.

The following examples illustrate the invention. They should not be construed as in any way limiting the invention.

Examples

1. Particle Segregation as a Function of Particle Size

To determine if segregation is a function of the granule size of selected BIODAC® cellulosic granules (available from Kadant Grantek Inc., 607 Liberty Street, Green Bay, Wis. 54304-3705), sample mixtures of BIODAC® cellulosic granules and a $10^{-10}$-10 NPK fertilizer granule were prepared. In each sample, the fertilizer was present at a level of 85% by weight and the cellulosic granules were present at a level of 15% by weight. The following three sizes of BIODAC® granules were used:

10/30 mesh

12/20 mesh

20/50 mesh.

A particles size analysis was completed on the fertilizer and the cellulosic granules samples before they were blended together. The results were as follows:

| US MESH | FERTILIZER | BIODAC 10/30 | BIODAC 12/20 | BIODAC 20/50 |
|---|---|---|---|---|
| +8 | 46.0% | 0.0% | 0.0% | 0.0% |
| +12 | 41.4% | 20.4% | 0.0% | 0.0% |
| +16 | 7.5% | 50.0% | 30.6% | 0.0% |
| +20 | 2.6% | 25.0% | 56.1% | 1.7% |
| +30 | 1.0% | 4.6% | 12.8% | 54.8% |
| +40 | 0.5% | 0.0% | 0.6% | 35.1% |
| +50 | 0.0% | 0.0% | 0.0% | 8.2% |
| −50 | 1.0% | 0.0% | 0.0% | 0.2% |

Using the screen analysis above and a mixture ratio of 85:15 of fertilizer granules to cellulosic granules the screen analysis of the mixtures was calculated to be:

| US MESH | 10/30 PLUS FERTILIZER | 12/20 PLUS FERTILIZER | 20/50 PLUS FERTILIZER |
|---|---|---|---|
| +8 | 39.1% | 39.1% | 39.1% |
| +12 | 38.2% | 35.2% | 35.2% |
| +16 | 13.8% | 10.9% | 6.3% |
| +20 | 6.0% | 10.7% | 2.5% |
| +30 | 1.6% | 2.8% | 9.1% |
| +40 | 0.4% | 0.5% | 5.7% |
| +50 | 0.0% | 0.0% | 1.2% |
| −50 | 0.8% | 0.8% | 0.9% |

Visual inspection of the mixtures showed that the blends of 10/30 and 12/20 cellulosic granules did not segregate. While the 20/50 blends did show limited segregation with some cellulosic granules going to the bottom of the bag, 20/50 blends were still in an acceptable range.

A drop spreader test was run to determine the degree of segregation. In this test, the mixtures were placed in a fertilizer spreader at the recommended spreader setting and dropped on a clean cement slab. Three foot increments were marked and samples were collected and then screened to determine segregation. The full test results were as follows:

At 3 to 6 feet:

| 20/50-1 Screen Analysis | | |
|---|---|---|
| 8 | 34.4 | 33.3% |
| 12 | 30.3 | 29.3% |
| 16 | 5.9 | 5.7% |
| 20 | 3.2 | 3.1% |
| 30 | 14.5 | 14.0% |
| 40 | 10.5 | 10.2% |
| 50 | 3.4 | 3.3% |
| −50 | 1.2 | 1.2% |
| | 103.4 | 100.0% |

| 10/30-1 Screen Analysis | | |
|---|---|---|
| 8 | 29.2 | 37.2% |
| 12 | 26.8 | 34.1% |
| 16 | 12.0 | 15.3% |
| 20 | 6.5 | 8.3% |
| 30 | 2.2 | 2.8% |
| 40 | 0.7 | 0.9% |
| 50 | 0.3 | 0.4% |
| −50 | 0.8 | 1.0% |
| | 78.5 | 100.0% |

| 12/20-1 Screen Analysis | | |
|---|---|---|
| 8 | 32.2 | 36.9% |
| 12 | 28.7 | 32.9% |
| 16 | 10.7 | 12.3% |
| 20 | 11.5 | 13.2% |
| 30 | 3.3 | 3.8% |
| 40 | 0.4 | 0.5% |
| 50 | 0.0 | 0.0% |
| −50 | 0.4 | 0.5% |
| | 87.2 | 100.0% |

At 9 to 12 feet:

| 20/50-2 Screen Analysis | | |
|---|---|---|
| 8 | 33.6 | 39.7% |
| 12 | 25.2 | 29.8% |
| 16 | 4.4 | 5.2% |
| 20 | 2.3 | 2.7% |
| 30 | 10.1 | 11.9% |
| 40 | 6.7 | 7.9% |
| 50 | 1.8 | 2.1% |
| −50 | 0.5 | 0.6% |
| | 84.6 | 100.0% |

| 10/30-2 Screen Analysis | | |
|---|---|---|
| 8 | 28.7 | 40.8% |
| 12 | 26.5 | 37.6% |
| 16 | 9.1 | 12.9% |
| 20 | 3.8 | 5.4% |
| 30 | 1.3 | 1.8% |
| 40 | 0.4 | 0.6% |
| 50 | 0.0 | 0.0% |
| −50 | 0.6 | 0.9% |
| | 70.4 | 100.0% |

| 12/20-2 Screen Analysis | | |
|---|---|---|
| 8 | 30.2 | 40.3% |
| 12 | 24.8 | 33.1% |
| 16 | 8.5 | 11.3% |
| 20 | 8.7 | 11.6% |
| 30 | 2.4 | 3.2% |
| 40 | 0.00 | 0.0% |

-continued

12/20-2 Screen Analysis

| | | |
|---|---|---|
| 50 | 0.0 | 0.0% |
| −50 | 0.3 | 0.4% |
| | 74.9 | 100.0% |

At 15 to 18 feet:

20/50-3 Screen Analysis

| | | |
|---|---|---|
| 8 | 36.4 | 39.6% |
| 12 | 27.7 | 30.1% |
| 16 | 4.8 | 5.2% |
| 20 | 2.7 | 2.9% |
| 30 | 11.0 | 12.0% |
| 40 | 6.9 | 7.5% |
| 50 | 2.0 | 2.2% |
| −50 | 0.5 | 0.5% |
| | 92.0 | 100.0% |

10/30-3 Screen Analysis

| | | |
|---|---|---|
| 8 | 28.6 | 43.8% |
| 12 | 23.5 | 36.0% |
| 16 | 8.0 | 12.3% |
| 20 | 3.4 | 5.2% |
| 30 | 1.2 | 1.8% |
| 40 | 0.2 | 0.3% |
| 50 | 0.0 | 0.0% |
| −50 | 0.4 | 0.6% |
| | 65.3 | 100.0% |

12/20-3 Screen Analysis

| | | |
|---|---|---|
| 8 | 28.0 | 40.8% |
| 12 | 23.4 | 34.1% |
| 16 | 7.5 | 10.9% |
| 20 | 7.3 | 10.6% |
| 30 | 2.0 | 2.9% |
| 40 | 0.2 | 0.3% |
| 50 | 0.0 | 0.0% |
| −50 | 0.2 | 0.3% |
| | 68.5 | 100.0% |

The averages vs. the calculated screen analysis are listed below.

| US MESH | 10/30 PLUS FERTILIZER | 10/30 CALCULATED | 12/20 PLUS FERTILIZER | 12/20 CALCULATED | 20/50 PLUS FERTILIZER | 20/50 CALCULATED |
|---|---|---|---|---|---|---|
| +8  | 40.6% | 39.1% | 39.4% | 39.1% | 37.5% | 39.1% |
| +12 | 35.9% | 38.2% | 33.4% | 35.2% | 29.7% | 35.2% |
| +16 | 13.5% | 13.8% | 11.5% | 10.9% | 5.4%  | 6.3%  |
| +20 | 6.3%  | 6.0%  | 11.8% | 10.7% | 2.9%  | 2.5%  |
| +30 | 2.2%  | 1.6%  | 3.3%  | 2.8%  | 12.6% | 9.1%  |
| +40 | 0.6%  | 0.4%  | 0.3%  | 0.5%  | 8.5%  | 5.7%  |
| +50 | 0.1%  | 0.0%  | 0.0%  | 0.0%  | 2.5%  | 1.2%  |
| −50 | 0.8%  | 0.8%  | 0.4%  | 0.8%  | 0.8%  | 0.9%  |

The results reported in the table above shows that the 10/30 and 12/20 mixtures do not significantly segregate and that only the 20/50 mixture segregation of the cellulosic and fertilizer granules occurs only to a limited (and acceptable) degree.

2. Particle Segregation Due to Blending, Bagging or Shipping

An 8-10-10 fertilizer blend derived from monoammonium phosphate, sulfur coated urea, and muriate of potash was combined with cellulosic particles. Cellulosic particles were dyed a bright blue color and added to the blend at a level of about 10% on a weight-to-weight basis. The formulation was bagged in 50 pound bags and the bags were palletized, stretch wrapped, and shipped by truck from Florida to central Minnesota. The pallet and bags were received in good condition in central Minnesota.

The bags of fertilizer/cellulosic particle blends were numbered 1-3, and the bags were sampled for particle segregation by removing 150 cc of product from six locations (samples labeled A-F) within each bag, using a granular fertilizer sample probe, and the samples were labeled A-F. The six locations were randomly selected from the top, sides and bottoms of the bags. The samples were individually bagged and then run through a set of sieves, sized # 14 through # 24 to determine if the particle size ratios varied based on the location in bag from which the sample were removed. A significant variation in particle size would indicate segregation of the particles during the blending, bagging or shipping.

The following table shows the results of this bag-sampling test.

TABLE 1

Bag Segregation Test

| Bag #1 Sieve Size | Sample A grams | % | Sample B grams | % | Sample C grams | % |
|---|---|---|---|---|---|---|
| 24 | 1.8 | 1.8 | 2.1 | 2.2 | 2.0 | 2.0 |
| 20 | 3.2 | 3.2 | 3.9 | 4.1 | 3.7 | 3.7 |
| 18 | 6.9 | 7.0 | 7.7 | 8.1 | 8.2 | 8.2 |
| 16 | 22.5 | 22.7 | 21.2 | 22.3 | 23.1 | 23.2 |
| 14 | 64.8 | 65.3 | 60.1 | 63.3 | 62.4 | 62.8 |
| Total | 99.2 | 100.0 | 95.0 | 100.0 | 99.4 | 100.0 |

TABLE 1-continued

Bag Segregation Test

| Bag #1 Sample D grams | % | Sample E grams | % | Sample F grams | % | LSD* | LSD |
|---|---|---|---|---|---|---|---|
| 2.4 | 2.3 | 1.7 | 1.8 | 1.9 | 1.9 | NS* | NS |
| 4.1 | 4.0 | 3.2 | 3.3 | 3.7 | 3.8 | NS | NS |
| 8.6 | 8.3 | 7.3 | 7.6 | 7.5 | 7.7 | NS | NS |
| 24.2 | 23.4 | 22.9 | 23.7 | 22.9 | 23.4 | NS | NS |
| 63.9 | 61.9 | 61.5 | 63.7 | 62.0 | 63.3 | NS | NS |
| 103.2 | 100.0 | 96.6 | 100.0 | 98.0 | 100.0 | | |

| Bag #2 Sieve Size | Sample A grams | % | Sample B grams | % | Sample C grams | % | LSD |
|---|---|---|---|---|---|---|---|
| 24 | 2.7 | 2.6 | 2.1 | 2.1 | 3.1 | 3.0 | NS |
| 20 | 4.2 | 4.0 | 3.7 | 3.6 | 2.9 | 2.8 | NS |
| 18 | 6.8 | 6.5 | 7.9 | 7.7 | 6.9 | 6.7 | NS |
| 16 | 24.8 | 23.7 | 26.1 | 25.5 | 25.2 | 24.6 | NS |
| 14 | 66.1 | 63.2 | 62.4 | 61.1 | 64.2 | 62.8 | NS |
| Total | 104.6 | 100.0 | 102.2 | 100.0 | 102.3 | 100.0 | |

| Bag #2 Sample D grams | % | Sample E grams | % | Sample F grams | % | LSD |
|---|---|---|---|---|---|---|
| 2.9 | 2.8 | 2.9 | 2.9 | 3.3 | 3.1 | NS |
| 3.7 | 3.6 | 3.9 | 3.9 | 4.8 | 4.5 | NS |
| 8.0 | 7.7 | 7.5 | 7.4 | 7.0 | 6.5 | NS |
| 23.1 | 22.3 | 25.9 | 25.6 | 26.3 | 24.5 | NS |
| 66.0 | 63.6 | 61.0 | 60.3 | 66.0 | 61.5 | NS |
| 103.7 | 100.0 | 101.2 | 100.0 | 107.4 | 100.0 | |

| Bag #3 Sieve Size | Sample A grams | % | Sample B grams | % | Sample C grams | % |
|---|---|---|---|---|---|---|
| 24 | 3.3 | 3.2 | 2.9 | 2.7 | 1.7 | 1.7 |
| 20 | 4.0 | 3.8 | 3.2 | 3.0 | 4.1 | 4.2 |
| 18 | 6.7 | 6.4 | 7.2 | 6.8 | 7.3 | 7.4 |
| 16 | 22.9 | 22.0 | 24.2 | 22.7 | 23.6 | 23.9 |
| 14 | 67.1 | 64.5 | 68.9 | 64.8 | 62.0 | 62.8 |
| Total | 104.0 | 100.0 | 106.4 | 100.0 | 98.7 | 100.0 |

| Bag #3 Sample D grams | % | Sample E grams | % | Sample F grams | % | LSD | LSD |
|---|---|---|---|---|---|---|---|
| 2.8 | 2.8 | 2.6 | 2.5 | 2.1 | 2.1 | NS | NS |
| 3.2 | 3.2 | 3.9 | 3.7 | 3.0 | 3.0 | NS | NS |
| 6.9 | 6.9 | 7.5 | 7.2 | 6.2 | 6.2 | NS | NS |
| 22.1 | 22.3 | 24.2 | 23.2 | 23.2 | 23.3 | NS | NS |
| 64.3 | 64.8 | 66.1 | 63.4 | 65.2 | 65.4 | NS | NS |
| 99.3 | 100.0 | 104.3 | 100.0 | 99.7 | 100.0 | | |

* "LSD" means least significant difference and "NS" means not significant.

The above data demonstrates that there was no significant separation or segregation of the cellulosic and fertilizer granules.

Also, the contents of the bags were visually examined. The blue colored cellulosic granules appeared to be uniformly distributed throughout the combination product in the bag.

The selected bags were then resealed and turned over several times and reexamined. Again, the mixture did not appear to visually change. As noted above, the particle size of the cellulosic granules was smaller than that of the fertilizer granules and this was visually discernable. Thus, although the cellulosic particles were substantially smaller and less dense (e.g., about 42-48 lb./ft$^3$ vs 50-56 lb./ft.$^3$) than the fertilizer particles there was no evident physical segregation of particles of different sizes and different bulk densities.

Additionally, to determine whether particle segregation was occurring during blending, bagging or shipping, the relative particle size ratios were analyzed to determine whether there were significant differences in these ratios between the six samples removed from each of the three bags. This data demonstrated that there were no significant differences in relative ratio for the different particle sizes indicating that no significant segregation was taking place within the bags.

3. Particle Segregation During Spreader Application

This example was directed to determining whether segregation between cellulosic granules and fertilizer granules in a heterogeneous blend is enhanced when a bag of the combination product is poured into a broadcast spreader that uses agitation to drop the product onto an impeller for spreading.

As noted above, segregation of the granules could have a detrimental effect on the activity of a pesticide or other active ingredients by concentrating it in areas and causing phytotoxicity in those areas while missing other areas to produce uneven control of targeted pests or plants.

In this example a commercial broadcast spreader, Scott's Proturf R8A was used. Three bags of blended fertilizer and cellulosic particles were selected from the pallet of products described in Example 1. The spreader was filled and application made on a clean concrete floor. Each spreader pass was fifty feet long and three passes were made with attention given to maintaining proper overlap between spreader passes. The spreader setting was selected to deliver one half pound of nitrogen for 1,000 square feet in accordance with the manufacturer's suggested spreader setting.

Following the application, the field of application (on the concrete floor) was divided into a series of grids 10.5 feet× 10.5 feet in size. The product was carefully swept up from each of seven grid sections and bagged. This was repeated for each of three different bags. Each individual grid sample was run through a series of sizing sieves sized #14 through #24 to determine whether the granular application was uniform or if segregation was taking place during the application process. If the relative ratios of granule sizes varied depending on where in the application grid the sample was removed, this would indicate that segregation occurred during the spreader application. For example, if larger granules were being thrown further than the smaller particles, there would be an abundance of larger granules in grids along the edges of the application area. Also, if granules were separating by size and density during agitation within the spreader hopper, the granule size ratio would be skewed toward an abundance of small granules in the sections of the grid.

The following table shows particle size ratio for each 110 square foot grid samples. The samples are labeled A-G and the sample bags are labeled 1-3.

Biodac Dust-Free Granule Segregation Project

TABLE 2

| Spreader Segregation Data | | | | | | | | |
|---|---|---|---|---|---|---|---|---|
| Bag #1 Sieve Size | Sample A grams | % | Sample B grams | % | Sample C grams | % | Sample D grams | % |
| 24 | 6.4 | 2.2 | 8.1 | 2.7 | 7.8 | 2.6 | 8.4 | 2.8 |
| 20 | 11.1 | 3.8 | 11.3 | 3.7 | 12.4 | 4.1 | 11.1 | 3.7 |
| 18 | 21.8 | 7.4 | 23.1 | 7.6 | 22.8 | 7.5 | 21.5 | 7.1 |
| 16 | 63.7 | 21.6 | 62.9 | 20.6 | 64.2 | 21.1 | 61.4 | 20.4 |
| 14 | 191.7 | 65.0 | 199.5 | 65.4 | 196.9 | 64.7 | 199.1 | 66.0 |
| Total | 294.7 | 100.0 | 304.9 | 100.0 | 304.1 | 100.0 | 301.5 | 100.0 |
| Bag #1 Sieve Size | Sample E grams | % | Sample F grams | % | Sample G grams | % | LSD | |
| 24 | 6.5 | 2.1 | 8.1 | 2.7 | 7.8 | 2.6 | NS | |
| 20 | 12.1 | 3.9 | 10.9 | 3.6 | 11.5 | 3.8 | NS | |
| 18 | 22.9 | 7.4 | 21.1 | 7.1 | 22.4 | 7.4 | NS | |
| 16 | 63.5 | 20.7 | 63.2 | 21.1 | 64.8 | 21.3 | NS | |
| 14 | 202.4 | 65.8 | 195.6 | 65.4 | 197.6 | 65.0 | NS | |
| Total | 307.4 | 100.0 | 298.9 | 100.0 | 304.1 | 100.0 | | |
| Bag #2 Sieve Size | Sample A grams | % | Sample B grams | % | Sample C grams | % | Sample D grams | % |
| 24 | 7.1 | 2.4 | 8.6 | 2.8 | 6.8 | 2.3 | 7.7 | 2.5 |
| 20 | 11.4 | 3.9 | 10.9 | 3.6 | 10.4 | 3.5 | 11.4 | 3.7 |
| 18 | 20.8 | 7.0 | 24.1 | 7.9 | 21.8 | 7.2 | 23.2 | 7.5 |
| 16 | 61.2 | 20.7 | 63.4 | 20.8 | 62.2 | 20.7 | 64.1 | 20.8 |
| 14 | 195.3 | 66.0 | 198.2 | 64.9 | 199.8 | 66.4 | 201.5 | 65.4 |
| Total | 295.8 | 100.0 | 305.2 | 100.1 | 301.0 | 100.0 | 307.9 | 100.0 |
| Bag #2 Sieve Size | Sample E grams | % | Sample F grams | % | Sample G grams | % | LSD | |
| 24 | 8.2 | 2.7 | 7.5 | 2.5 | 6.5 | 2.1 | NS | |
| 20 | 10.8 | 3.5 | 12.1 | 4.0 | 11.6 | 3.8 | NS | |
| 18 | 21.8 | 7.1 | 22.1 | 7.3 | 23.5 | 7.8 | NS | |
| 16 | 64.2 | 21.0 | 61.1 | 20.3 | 66.2 | 21.8 | NS | |
| 14 | 200.8 | 65.7 | 198.2 | 65.8 | 195.4 | 64.4 | NS | |
| Total | 305.8 | 100.0 | 301.0 | 100.0 | 303.2 | 100.0 | | |
| Bag #3 Sieve Size | Sample A grams | % | Sample B grams | % | Sample C grams | % | Sample D grams | % |
| 24 | 7.3 | 2.4 | 9.2 | 3.1 | 7.9 | 2.6 | 7.1 | 2.4 |
| 20 | 12.4 | 4.2 | 11.8 | 3.9 | 12.1 | 4.0 | 11.7 | 3.9 |
| 18 | 22.3 | 7.5 | 22.1 | 7.3 | 24.1 | 8.0 | 23.4 | 7.7 |

TABLE 2-continued

Spreader Segregation Data

| 16 | 61.9 | 20.8 | 64.2 | 21.3 | 66.2 | 22.0 | 61.1 | 20.2 |
|---|---|---|---|---|---|---|---|---|
| 14 | 194.2 | 65.1 | 194.2 | 64.4 | 190.1 | 63.3 | 198.7 | 65.8 |
| Total | 298.1 | 100.0 | 301.5 | 100.0 | 300.4 | 100.0 | 302.0 | 100.0 |

| Bag #3 Sieve Size | Sample E grams | % | Sample G grams | % | Sample F grams | % | LSD |
|---|---|---|---|---|---|---|---|
| 24 | 6.9 | 2.2 | 7.6 | 2.5 | 8.1 | 2.6 | NS |
| 20 | 10.9 | 3.5 | 11.4 | 3.8 | 12.4 | 4.0 | NS |
| 18 | 20.9 | 6.8 | 22.1 | 7.3 | 24.7 | 8.0 | NS |
| 16 | 66.1 | 21.5 | 61.5 | 20.3 | 63.2 | 20.6 | NS |
| 14 | 203.1 | 66.0 | 200.9 | 66.2 | 199.1 | 64.7 | NS |
| Total | 307.9 | 100.0 | 303.5 | 100.0 | 307.5 | 100.0 | |

As already explained, there was a significant difference in relative granule size ratio between the cellulosic granules and the fertilizer granules within the blended combination product. The larger sized granules (#14 and #16), were composed primarily of fertilizer nutrients while the smaller sized granules (#18, #20 and #24), were composed primarily of cellulosic granules.

The above data demonstrates that there was no significant difference in the relative ratio of particles within the application field regardless of where the grid sample was taken. These results thus demonstrate that the cellulosic granules, can be blended with fertilizer granules of a different size without significant granule segregation occurring. This example also demonstrates that cellulosic particles are an excellent carrier for pesticides and other active ingredients that require good particle distribution on soil as well effective contact with plant leaf surfaces.

4. Cellulosic Particle Distribution Per Unit Area

Since it is intended that the cellulosic granules carry pesticides and other active ingredients, it is important to determine if the minimum number of cellulosic granules per unit area required are being delivered to produce the desired levels of actives activity. To determine the number of cellulosic granules per unit area, a volume of the combination product was poured into a commercial broadcast fertilizer spreader. The spreader was set to deliver one pound of nitrogen per 1,000 square feet. Three passes of the spreader were made at 50 foot lengths with attention to maintaining correct overlap between the passes. Following the application, a ring with an internal surface area of 0.75 square feet was randomly placed over the treated area and individual cellulosic granules were counted in each ring. Fourteen ring area samples were evaluated for each of three separate 50 pound bags of fertilizer. The results of this study appear below in Table 3.

TABLE 3

Cellulosic Dust Free Particle Distribution

| Sample | Bag #1 | Cellulosic Particles/ 0.75 Sq Ft Bag #2 | Bag #3 |
|---|---|---|---|
| A | 18 | 12 | 18 |
| B | 14 | 18 | 21 |
| C | 16 | 19 | 22 |
| D | 12 | 15 | 15 |
| E | 19 | 16 | 16 |
| F | 13 | 12 | 14 |
| G | 16 | 21 | 19 |
| H | 19 | 12 | 18 |
| I | 11 | 19 | 21 |
| J | 14 | 22 | 16 |
| K | 24 | 19 | 18 |
| L | 17 | 13 | 12 |
| M | 16 | 13 | 15 |
| N | 19 | 21 | 18 |

The data above indicates that the number of cellulosic granules per unit area remained relatively uniform and consistent. The cellulosic granule numbers per 0.75 square feet of application area ranged from a minimum of 16 granules to a maximum of 24 granules. This would be adequate for pre-emergence and post-emergence pesticides commonly used in the turf grass industry and related applications including home, lawn and garden, and crop.

Of course, the number of granules per unit area required to obtain the desired actives effect will vary with the types of actives material. For example, highly soluble or volatile pesticide or other active ingredients will require fewer particles per square foot to produce acceptable efficacy. Active ingredients that are relatively insoluble in water or post-emergence herbicide products will require more particles per unit area to obtain a desired efficiency.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of making a heterogeneous blend of fertilizer granules and absorbent cellulosic granules carrying one or more active ingredients that resists segregation of the cellulosic and fertilizer granules and the formation of active ingredient dust comprising:
   providing about 5 to 90% by weight cellulosic granules and about 95 to 10% by weight fertilizer granules;
   treating the cellulosic granules with one or more active ingredients; and
   generally uniformly blending the treated cellulosic granules and the fertilizer granules.

2. The method of claim 1 in which the active ingredients are pesticidal ingredients.

3. The method of claim 1 in which the cellulosic granules are treated by spraying the granules with the active ingredients in liquid form at a level up to the liquid holding capacity of the granules.

4. The method of claim 1 in which the active ingredients are applied to the cellulosic granules in dried powder form.

5. The method of claim 4 in which the granules are coated with an adherent liquid after the active ingredients are applied.

6. A method of making a heterogeneous blend of fertilizer granules and absorbent cellulosic granules where the cellulosic granules selectively carry one or more active ingredients, the fertilizer granules are substantially free of the active ingredients, and the blend resists segregation of the cellulosic and fertilizer granules and formation of active ingredient dust comprising:
   providing cellulosic granules and fertilizer granules;
   blending about 5 to 90% by weight cellulosic granules with about 95 to 10% by weight fertilizer granules;
   providing one or more active ingredients in liquid form; and
   spraying the blend with the one or more liquid active ingredients to achieve selective absorption of the active ingredients by the cellulosic granules with little or none of the active ingredients remaining on the fertilizer granules.

7. The method of claim 6 in which after the blend is sprayed with the liquid active ingredient(s), the blend is sprayed with an oil.

8. The method of claim 6 in which the active ingredients are chosen from the group consisting of herbicides, fungicides, insecticides, wetting agents, microorganisms/micronutrients, biostimulants, root stimulants and industrial and turf related enzymes.

9. The method of claim 6 in which the cellulosic granules are derived from pulp or paper sludge.

10. The method of claim 6 in which the cellulosic granules are treated with a herbicide chosen from the group consisting of benefin, flumioxazin, dithiopyr, oxadiazon, pendimethalin, penoxsulam, trifluralin and trifluralin/benefin.

11. The method of claim 10 in which the herbicide is oxadiazon.

12. The method of claim 6 in which the cellulosic granules are treated with an insecticide chosen from the group consisting of bifenthrin, cadusafos, cyfluthrin, chloropyrifor, ethoprop, fipronil, halofenozide, imidacloprid, methoprene, permethrin, phorate, temephos and terbufos.

13. The method of claim 6 in which the cellulosic granules are treated with a fungicide chosen from the group consisting of azoxystrobin, tebuconazole, or propiconazole.

14. The method of claim 6 in which the cellulosic granules have a density of about 30-48 pounds per cubic foot.

15. The method of claim 6 in which the cellulosic granules are of a size chosen from the group consisting of 4/8, 4/30, 10/30, 12/20, 16/30, 20/50 and 30/60 and any combination thereof.

16. The method of claim 6 in which the cellulosic granules are treated with from about 0.1 to 25% by weight of active ingredient(s).

17. The method of claim 6 in which the fertilizer granules are chosen from the group consisting of sulfur/swelling clay matrices, ammonium sulfate, urea, potash, ammonium phosphate and micronutrient fertilizers.

18. The method of claim 6 in which the active ingredients are pesticidal ingredients.

* * * * *